United States Patent [19]
Antos

[11] 3,992,268
[45] Nov. 16, 1976

[54] HYDROCARBON CONVERSION PROCESS

[75] Inventor: George Antos, Arlington Heights, Ill.

[73] Assignee: Universal Oil Products Company, Des Plaines, Ill.

[22] Filed: Nov. 18, 1974

[21] Appl. No.: 524,844

[52] U.S. Cl. ................................. 204/72; 204/79
[51] Int. Cl.² ...................... C25B 3/00; C25B 3/10
[58] Field of Search ............... 204/72, 73 R, 78–80

[56] References Cited
UNITED STATES PATENTS

| | | | |
|---|---|---|---|
| 2,867,569 | 1/1959 | Kronenthal | 204/72 |
| 3,228,799 | 1/1966 | Rohrback | 136/100 |
| 3,383,309 | 5/1968 | Chandler | 210/11 |
| 3,476,803 | 11/1969 | Pine | 260/676 R |
| 3,502,559 | 3/1970 | Alexander | 204/195 B |
| 3,640,846 | 2/1972 | Johnson | 195/27 |
| 3,711,392 | 1/1973 | Metzger | 204/180 P |

OTHER PUBLICATIONS

Trans. Electrochem. Soc., vol. 75, pp. 333–337 (1939) by Glasstone et al.

*Primary Examiner*—F.C. Edmundson
*Attorney, Agent, or Firm*—James R. Hoatson, Jr.; Raymond H. Nelson; William H. Page, II

[57] ABSTRACT

A process for the production of hydrocarbonaceous materials which comprises reacting waste materials with a microorganism to produce organic products and treating the resultant organic products by electrolysis to form hydrocarbonaceous materials and carbon dioxide is disclosed.

9 Claims, No Drawings

HYDROCARBON CONVERSION PROCESS

This invention relates to a process for the production of hydrocarbon materials. More specifically, this invention relates to a process for the preparation of hydrocarbon materials which comprises reacting waste materials with a microorganism to produce organic products and treating the organic products in an electrochemical cell to produce hydrocarbon materials and a gas comprising carbon dioxide.

It has been shown in the prior art that waste materials may be utilized to prepare hydrocarbonaceous materials in a reaction process in which extremely high temperatures and pressures are utilized. It is also known in the art that waste materials may be treated with microorganisms as is common in various sewage and sewage sludge plants, that carboxylic acids may be decarboxylated to the corresponding saturated or unsaturated hydrocarbon by use of pressure, temperature and a suitable decarboxylation catalyst and that various carboxylic acids may be decarboxylated by treatment in an electrochemical cell, said electrochemical process commonly known as the Kolbe electrolysis.

In contradistinction to the prior art it has now been discovered that a process for the preparation of hydrocarbon materials may be performed which comprises reacting waste materials with a microorganism to produce organic products, particularly carboxylic acids, and treating the resultant organic products in an electrochemical cell to produce hydrocarbon materials and a gas comprising carbon dioxide. The utilization of the present invention will allow the manufacturer a more inexpensive method for the production of the hydrocarbon materials as a result of the utilization of lower temperatures and pressures compared with those currently in use in pyrolysis techniques. The manufacturer will also have the benefit of performing the preparation of the hydrocarbon materials in either an anaerobic or aerobic atmosphere is which the types of organic products produced from the reaction of the waste materials and the microorganisms are controlled to a greater degree of precision. The utilization of the above cited invention will also allow the manufacturer of the hydrocarbon materials to possess a greater control over both the type and length of chain of hydrocarbon materials prepared as a result of the various microorganisms and electrochemical cell parameters which may be employed. Examples of electrochemical cell parameter which may be employed in the utilization of the present invention will include current density, anodic material, the pH of the electrolyte, solvent and temperature. The utilization of the above set forth invention will also make available to the manufacturer a source of sulfur-free hydrocarbon materials which may be easily converted into gasoline or heating oil. Nationally, the utilization of the above set forth invention will allow for a greater United States independence of energy resources in compliance with the national effort to become energy independent by the year 1980.

The desired products of the process of this invention, namely, hydrocarbon materials are utilized in the chemical industry in many ways. For example, hydrocarbon materials may be refined or used as gasoline or heating oil; in the manufacture of candles; as alkylating agents; as solvents for other chemicals such as the use of isooctane (2,2,4-trimethylpentane); or a starting material for the production of other chemicals and products.

It is therefore and object of this invention to provide a process for the preparation of hydrocarbon materials.

A further object of this invention is to provide a process for the preparation of hydrocarbon materials using certain microorganisms and electrochemical cells which will permit the recovery of the desired hydrocarbon materials in a more expedient manner.

In one aspect an embodiment this invention resides in a process for the preparation of hydrocarbon materials which comprises reacting waste materials with a microorganism at reaction conditions in an aerobic or anaerobic atmosphere to produce organic products, electrolyzing the resultant organic products in an electrochemical cell at electrolysis conditions to produce hydrocarbon materials and a gas comprising carbon dioxide and recovering the resultant hydrocarbon materials.

A specific embodiment of this invention resides in a process for preparing hydrocarbon materials having a chain length of from about 1 to about 15 carbon atoms whereby the chain length is saturated, which comprises reacting dewatered human waste with a microorganism from the genus *Butyribacterium* at a reaction temperature of from about 25° C to about 100° C. and an anaerobic atmosphere (absence of free oxygen) to produce various carboxylic acids and treating the resultant carboxylic acid products in an electrochemical cell which consists of an anode comprising platinum, a cathode comprising platinum, an electrolyte which is acidic in nature and a solvent comprising methanol at an electrolysis temperature of from about 50° C to about 200° C. and a pressure of 1 atmosphere, and recovering the resultant hydrocarbon material having a chain length of from about 1 to about 15 carbon atoms, said hydrocarbon material being predominantly saturated compounds.

A second specific embodiment of this invention resides in a process for preparing a hydrocarbon material having from between 1 to about 15 carbon atoms which comprises reacting dewatered animal waste with a microorganism from the genus of *Propionibacterium* at a temperature of 50° C. and an anaerobic atmosphere (absence of free oxygen) to produce carboxylic acids possessing chain lengths from about 1 to about 15 carbon atoms in length and treating said produced carboxylic acids in an electrochemical cell which consists of an anode comprising iridium a cathode comprising platinum, an electrolyte which is acidic in nature and a solvent comprising N, N'-dimethylformamide at an electrolysis temperature of 250° C. and a pressure of 50 atmospheres afforded by the introduction of a substantially inert gas such as nitrogen and recovering the resultant hydrocarbon material having from about 1 to about 15 carbon atoms, said hydrocarbon material being predominantly saturated.

Other objects and embodiments will be found in the following further detailed description of the present invention.

As hereinbefore set forth, the present invention is concerned with a process for preparing hydrocarbon materials which comprises reacting waste materials with a microorganism to produce organic products, predominantly carboxylic acids, and treating the resultant organic products in an electrochemical cell to produce hydrocarbon material and a gas comprising carbon dioxide. The reaction of the waste products with a microorganism is effected under reaction conditions which include a temperature of from about 25° C to about 250° C. in an atmosphere which is either aerobic or anaerobic in nature. The treatment of the resultant organic products in the electrochemical cell is effected at electrolysis conditions which include a temperature of from about 15° C to about 500° C. and a pressure of from about 1 atmosphere to about 100 atmospheres. When superatmospheric pressures are employed, said pressure is afforded by the introduction of a substantially inert gas such as nitrogen or helium to the reaction or an electrochemical zone.

Examples of suitable waste material which may be utilized as one of the starting materials of the present invention will include solid human waste, solid animal waste, rubbish, "household" garbage, industrial garbage, industrial wastes and unwanted by-products, sewage, sewage sludge, etc.

Suitable examples of microorganisms which may be utilized in the process of the present invention include bacteria, yeasts, molds and protozoa. The types of bacteria which may be utilized include genera such as *Propionibacterium, Butyribacterium, Microbacterium, Corynebacturium, Listeria, Lactobacillus, Brevibacterium, Kurthia, Clostridium, Micrococcus, Staphylococcus, Gaffkya, Sarcina, Diplococcus, Streptococcus, Leuconostoc, Neisseria, Veillonella, Azotobacter, Rhizobium, Alcaligenes, Achromobacter, Flavobacterium, Escherichia, Aerobacter, Klebsiella, Paracolobactrum, Erwinia, Proteus, Salmonella, Shigella, Pasteurella, Brucella, Haemophilus, Bacteroides, Fusobacterium*, etc.

Specific examples of yeasts contemplated within the scope of this invention would include the genera *Candida, Cryptococcus, Nematospora, Lipomyces, Saccharomyces, Schizosaccharomyces*, etc. Suitable examples of molds would include the genera *Cryptococcus, Fusarium, Penicillium, Neurospora, Rhizopus, Sapromyces*, etc. Suitable examples of protozoa would include the genera *Amoeba, Euglena, Paramecium, Badhamia*, etc.

Suitable examples of carboxylic acids which may be produced from the reaction of the waste material with the microorganism will include all carboxylic acids and polycarboxylic acids possessing of from about 1 carbon atom to about 20 carbon atoms or more. Specific examples of said carboxylic acids would include acetic acid, propionic acid, butyric acid, isobutyric acid, n-valeric acid, trimethylacetic acid, caproic acid, n-heptylic acid caprylic acid, pelargonic acid, decanoic acid, undecanoic acid, dodecanoic acid, tridecanoic, tetradecanoic acid, pentadecanoic acid, heptadecanoic acid, octadecanoic acid, nonadecanoic acid, eicodecanoic acid, etc.

The electrolysis of the organic products, which are predominantly carboxylic acids in nature, may be performed in an electrochemical cell in an electrochemical process commonly known as the Kolbe reaction, which is the anodic formation of products through intervention of both radical and carbonium ion species. The physical parameters which will effect the electrolysis of the carboxylic acids to form the hydrocarbon materials and a gas comprising carbon dioxide will be the pH of the electrolyte, temperature, solvent and the influence of any foreign electrolytes present during electrolysis. The electrolysis may be performed in either an aqueous electrolyte or an organic electrolyte depending upon the specific hydrocarbonaceous materials which are desired from the electrolysis of the carboxylic acids. In both an aqueous or non-aqueous electrolyte either platinum or iridium may be utilized as the anode which will support the formation of radical and/or cationic intermediates from the carboxylate ions. It is also contemplated within the scope of this electrolysis process that gold, nickel and platinized platinum electrodes may also be utilized although not necessarily with equivalent results. It should be noted, however, that in non-aqueous slovents the choice of the anodic material is less critical than the choice in the aqueous electrolyte, although in both aqueous solvents a smooth platinum anode is preferred. It should be noted at this point that any foreign anodic ions present in the electrolyte will have the effect of forming a surface on the anode, especially the platinum anode, which will prevent maximum efficiency in the electrolysis process.

Another physical parameter which will effect the production of the resultant hydrocarbon materials and gases comprising carbon dioxide in the electrolytic cell is the effect of pH. When effecting the electrolysis in an organic solvent the pH should optimally be kept in the acidic range during the electrolysis. The acidic range may be effected by using a large excess of the carboxylic acid as compared to the carboxylate ion in the electrolyte cell. In contrast to the organic solvent when utilizing an aqueous solvent such as water, it may be necessary to employ a mercury cathode and fully neutralize the carboxylic acid in the aqueous solution to a pH of 7.5 to about 8. This method, commonly known as the salt deficit method may be employed where the carboxylic acid produced from the reaction of the microorganisms with the waste material produced a mixture of carboxylic acids of widely differing pK to effect the electrolysis preferentially of the stronger acid.

A third physical parameter in the conduct of the electrochemical process is the effect of the solvent. In aqueous electrochemical processes water is, of course, the preferred solvent. In non-aqueous electrochemical processes it has been found that alcohols such as methanol, ethanol, butanol, pentanol, hexanol, heptanol, octanol or nonanol may be utilized for the electrolysis. Another solvent which has been found extremely useful in the electrochemical process is N,N'-dimethylformamide which, however, is anodically oxidized itself.

A further physical parameter which may effect the production of the hydrocarbon materials and a gas comprising carbon dioxide is the effect of temperature. It has been shown through experimental work that an increase in the temperature of the electrochemical cell tends to decrease the yield of the resultant hydrocarbon materials and gas comprising carbon dioxide. It is contemplated within the scope of this invention that the electrochemical process may be conducted at a temperature in the extreme of 500° C. and a pressure of 100 atmospheres, although these conditions should be considered minimal to the production of the hydrocarbon material.

The microbial treatment of the waste material may be effected in an aqueous medium or any inert material be utilized as a medium such as n-pentane, n-hexane, 2,2,4-trimethylpentane (isooctane), benzene, toluene, xylene, etc. It is understood that the aformentioned waste materials, microorganisms, organic acids, anodic materials, solvents and mediums are only representative of the class of compounds which may be employed, and that the present invention is not necessarily limited thereto.

It is contemplated within the scope of this invention that the process for the preparation of the hydrocarbon materials may be performed in a continuous manner of operation. When such a type of operation is employed the reactants comprising the waste material and the microorganisms are charged to a reaction vessel at a predetermined condition of temperature and possessing either an anaerobic (free oxygen absent) or an aerobic (free oxygen present) atmosphere. After completion of the desired residence time the organic products produced, namely carboxylic acids, are continually withdrawn and subsequently charged to an electrochemical cell wherein they are electrolyzed to produce hydrocarbon materials and a gas comprising carbon dioxide. The electrochemical process may be performed for period of time from about 0.5 to about 25.0 hours or more at predetermined conditions of temperature and pressure. the hydrocarbon material formed in the electrolysis zone or cell is withdrawn as the electrolysis effluent while any unelectrolyzed organic products are recycled to the electrolysis zone or cell or to the first reaction zone and any unreacted microorganisms or waste material are recovered and recycled to the first reaction zone. It is also contemplated that the above set forth invention may be practiced in a batch type operation although the continuous method of operation is the desirable mode of operation.

Another feature of this invention is the inclusion of separation techniques to aid in optimum process operations. The products of the microbial treatment may be subjected to separation procedures in order to separate the carboxylic acids from other organic products prior to electrochemical treatment. Examples of these separation techniques may include solvent extraction, precipitation, complexation, acid base reaction, etc.

The following examples are given to illustrate the process of the present invention which, however, are not intended to limit the generally broad scope of the present invention in strict accordance therewith.

EXAMPLE I

In this example 0.5 grams of dewatered human waste and 0.05 grams of a microorganism consisting of *Butyribacterium rettgeri* are charged to a reaction zone maintained under an anaerobic atmosphere at a temperature of 27° C. The product is recovered from the reaction zone after a period of time comprising 2 hours and divided into two parts. The first part is analyzed by means of gel permeation chromatography and found to contain predominantly carboxylic acids possessing between 1 carbon atom and 21 carbon atoms. The second part of the sample is charged to an electrochemical cell comprising a smooth platinum wire as an anode, a platinum cathode, an amperemeter, a slidewire resistance, a d.c. power source, a methanol solvent and pH value of 6.5 for the methanolic electrolyte. The electrochemical cell is maintained at a predetermined temperature of 50° C. and a pressure of 1 atmosphere. The second portion of the organic products is electrolyzed for a period of time comprising 2 hours at which point in time the resultant product is removed and analyzed by means of gas-liquid chromatography instrumentation, said analysis dislosing the resultant product to be predominantly saturated hydrocarbon material possessing from 1 carbon atom to about 20 carbon atoms. The treated product is also analyzed for sulfur content, said analysis disclosing the reaction product to be sulfur-free.

EXAMPLE II

In this example 0.75 grams of dewatered animal waste and 0.03 grams of a microorganism consisting of *Propionibacterium freudenreichii* are charged to a reaction zone maintained under an anaerobic atmosphere at a temperature of 50° C. The product is recovered from the reaction zone after a period of time comprising 4 hours and divided into two parts. The first part is analyzed by means of gel permeation chromatography and found to contain predominantly carboxylic acids possessing between 1 carbon atom and 21 carbon atoms. The second part of this sample is charged to an electrochemical cell comprising a smooth iridium wire as an anode, a platinum cathode, an amperemeter, slidewire resistance, a d.c. power source an N,N-dimethylformamide solvents and a pH value of 5.0 for the N,N-dimethylformamidic electrolyte. The electrochemical cell is maintained at a predetermined temperature of 250° C. and a pressure of 50 atmospheres as afforded by the introduction of substantially inert nitrogen gas to the electrochemical cell. The second portion of the organic products is electrolyzed for a period of time comprising 1.5 hours at which point in time the resultant product is removed an analyzed by means of gas-liquid chromatography instrumentation, said analysis disclosing the resultant product to be predominantly saturated hydrocarbon material possessing from 1 carbon atom to about 20 carbon atoms. The treated product is also analyzed for sulfur-content, said analysis disclosed the reaction product to be sulfur-free.

EXAMPLE III

In this example 0.44 grams of sewage sludge and 0.07 grams of *Acetobacter aceti* are charged to a reaction zone maintained under an aerobic atmosphere at a temperature of 75° C. The reaction product is recovered from the reaction zone after a period of time comprising 4 hours of residence and divided into two parts. The first part is analyzed by means of gel permeation chromatography and found to contain predominantly carboxylic acids possessing from about 1 and 21 carbon atoms. The second part of the sample is charged to an electrochemical cell comprising a smooth platinum wire as an anode, an amperemeter, a slidewire resistance, a d.c. power source, an aqueous solvent comprising water and a pH value of 7.2 for the aqueous electrolyte. The electrochemical cell is maintained at a predetermined temperature of 50° C. and a pressure of 1 atmosphere with a mercury cathodic wire placed in the bottom of the cell. The second portion of the organic product is electrolyzed for a period of time comprising 5 hours at which point in time the resultant product is removed and analyzed by means of gas-liquid chromatography instrumentation, said analysis disclosing the resultant product to be predominantly saturated hydrocarbon material possessing from 1 to about 20 carbon atoms. The treated product is also analyzed for sulfur content, said analysis disclosing the reaction product to be sulfur-free.

I claim as my invention:

1. A process for the preparation of hydrocarbon materials which comprises;
    a. reacting waste materials with a microorganism in an aerobic or anaerobic atmosphere at conditions to produce carboxylic acids;
    b. electrolyzing the resultant acids in an electrochemical cell at electrolysis conditions to produce hydrocarbon materials and a gas comprising carbon dioxide; and
    c. recovering the resultant hydrocarbon materials.

2. The process of claim 1 further characterized in that the reaction conditions in step (a) include a temperature in the range of from about 15° to about 250°C.

3. The process of claim 1 further characterized in that the electrolysis conditions include a temperature in the range of from about 15° to about 500° C. and a pressure of from about atmospheric to about 100 atmospheres.

4. The process of claim 1 further characterized in that the microorganism is from the genus *Butyribacterium*.

5. The process of claim 1 further characterized in that the microorganism is from the genus *Propionibacterium*.

6. The process of claim 1 further characterized in that the microorganism is from the genus *Acetobacter*.

7. The process of claim 1 further characterized in that the electochemical cell comprises an anode comprising platinum, a cathode comprising platinum, an electrolyte which is acidic and a solvent comprising methanol.

8. The process of claim 1 further characterized in that the electrochemical cell comprises an anode comprising iriduim, a cathode comprising platinum, an electrolyte which is acidic and a solvent comprising N,N-dimethylformamide.

9. The process of claim 1 further characterized in that the electrochemical cell consists of an anode comprising platinum, a cathode comprising mercury, an elctrolyte which is neutral and a solvent comprising water.

* * * * *